United States Patent [19]
Garlich et al.

[11] Patent Number: 5,300,289
[45] Date of Patent: Apr. 5, 1994

[54] PHYTATE ANTIMICROBIAL COMPOSITIONS IN ORAL CARE PRODUCTS

[75] Inventors: Joseph R. Garlich; Tipton T. Masterson; R. Keith Frank, all of Lake Jackson, Tex.

[73] Assignee: The Dow Chemical Company, Midland, Mich.

[21] Appl. No.: 806,070

[22] Filed: Dec. 10, 1991

[51] Int. Cl.$^5$ ............................ A61K 7/16; A61K 7/22
[52] U.S. Cl. ........................................ 424/54; 424/49; 424/52; 424/57
[58] Field of Search ........................... 424/49-58

[56] References Cited

U.S. PATENT DOCUMENTS

| | | |
|---|---|---|
| 3,934,002 | 1/1976 | Haefele . |
| 4,193,988 | 3/1980 | Forward et al. . |
| 4,259,316 | 3/1981 | Nakashima et al. . |
| 4,263,276 | 4/1981 | Harvey . |
| 4,305,928 | 12/1981 | Harvey . |
| 4,332,791 | 6/1982 | Raaf et al. . |
| 4,335,102 | 6/1982 | Nakashima et al. . |
| 4,394,371 | 7/1983 | Barberio . |
| 4,528,181 | 7/1985 | Morton et al. . |
| 4,645,662 | 2/1987 | Nakashima et al. . |
| 4,795,628 | 1/1989 | Afseth ............................ 424/54 |
| 4,824,661 | 5/1989 | Wagner ........................... 424/52 |
| 4,826,675 | 5/1989 | Gaffar et al. . |
| 5,037,634 | 8/1991 | Williams et al. . |

FOREIGN PATENT DOCUMENTS

| | | |
|---|---|---|
| 0321180A1 | 6/1989 | European Pat. Off. . |
| 2918134 | 11/1979 | Fed. Rep. of Germany . |
| 61-200908 | 9/1986 | Japan . |
| 1384375 | 2/1975 | United Kingdom . |

OTHER PUBLICATIONS

H. Nordbo, "The Affinity of Chlorhexidine for Hydroxyapatite and Tooth Surfaces", Scan. J. Dent. Res., 80, 465–473 (1972).

H. Nordbo and G. Rolla, "Desorption of Salivary Proteins from Hydroxyapatite by Phytic Acid and Glycerophosphate and the Plaque-Inhibiting Effect of the Two Compounds In Vivo", J. Dent. Res., 51, 800–802 (1972).

D. S. Magrill, "The Effect of pH and of Orthophosphate on the Adsorption of Phytate by Hydroxyapatite During Prolonged Exposure", Archs oral Biol., 18, 1269–1273 (1973).

H. W. Kaufman and I. Kleinberg, "X-Ray Diffraction Study of the Effect of Phytate on the In Vitro Formation of Calcium Phosphates", J. Dent. Res., 52 (Special Issue), 169 (1973).

A. Gaffar and N. Rustogi, "Effects of Sodium Phytate and Benzethonium Chloride Rinses on Plaque Formation in Humans", Caries Res., 16, 472–474 (1982).

H. Nordbo and G. Rolla, "The Plaque-Inhibiting Capacity of Glycerophosphate and Phytic Acid", J. Dent. Res., 79, 507–509 (1971).

T. H. Grenby, "Trials of Three Organic Phosphorus-Containing Compounds as Protective Agents Against Dental Caries in Rats", J. Dent. Res., 52, 454–461 (1973).

M. F. Cole and W. H. Bowen, "Effect of Sodium Phytate on the Chemical and Microbial Composition of Dental Plaque in the Monkey", J. Dent. Res., 54, 449–457 (1975).

Primary Examiner—Shep K. Rose

[57] ABSTRACT

Oral compositions containing phytic acid or a physiologically acceptable salt thereof, a cationic antimicrobial compound and a compatibilizing agent are disclosed for controlling dental calculus, dental plaque, gingivitis, periodontitis and/or oral malodor.

32 Claims, No Drawings

PHYTATE ANTIMICROBIAL COMPOSITIONS IN ORAL CARE PRODUCTS

BACKGROUND OF THE INVENTION

The present invention relates to oral compositions containing an anticalculus or an antiplaque/antigingivitis agent.

"Oral composition" means a composition for topical applications to the oral cavity to clean and care for the teeth as well as the oral cavity surfaces. Representatives of such compositions are oral hygiene products and dentifrices such as mouthwashes or rinses, toothpaste, dental gels, tooth powder, chewing gum, lozenges, and similar products. In addition to cleaning teeth to remove dental plaque, the function of oral hygiene preparations is to stop the formation of dental calculus, to prevent dental disorders such as caries, periodontitis and gingivitis, and also to eliminate halitosis.

Dental calculus, or tartar as it is sometimes called, is a hard mineralized material which forms on teeth that consists of inorganic and organic components. The inorganic portion is largely calcium and orthophosphate arranged in a crystal lattice called hydroxyapatite (HAP). The organic portion is derived mainly from microorganisms (i.e., bacteria, yeast, etc.) as well as epithelial cells, white blood cells and food debris.

Formation of dental calculus occurs in two steps. In the first step, plaque is deposited on the teeth. "Plaque" consists of inorganic and organic components derived from saliva, food and bacteria which are present in the oral cavity. Most of the plaque consists of dead and living bacteria surrounded by a gel-like matrix derived from the bacteria and saliva. In the second phase, plaque undergoes calcification to form dental calculus. Initially, amorphous deposits of calcium phosphate begins to appear on and within the matrix of the dental plaque. As the aggregates of calcium phosphate become sufficiently closely packed together, they crystalize to form HAP. The amorphous calcium phosphate, although related to hydroxyapatite, differs from it in crystal structure, particle morphology and stoichiometry.

In addition to being an integral step for the formation of calculus, consequences of the presence of plaque include gingivitis, periodontitis, tooth decay (dental caries) and denture associated problems. Inhibition of oral bacteria involved in the formation of plaque by antimicrobials or antiseptic agents is one means to retard the formation of plaque, thus aiding in preventing or controlling the formation of calculus and other plaque related diseases; see, for example, P. S. Hull, *J. Clinical Periodontology*, 7, 431-442 (1980). Examples of antiseptic agents include bisbiguanides, such as chlorhexidine and alexidine, and numerous antibacterially active quaternary ammonium compounds, such as cetylpyridinium chloride or the quaternary ammonium compounds described in U.S. Pat. Nos. 3,369,046 and 4,820,507; and quaternary ammonium organosiloxane compounds described in U.S. Pat. No. 4,161,518.

Although the quaternary ammonium compounds are rapidly adsorbed to the tooth surfaces, they exhibit only a moderate degree of efficacy as antiplaque and antigingivitis agents as they are rapidly released from the tooth surface and thus retained in the oral cavity for only a short period of time. Chlorhexidine has been the most successful antiplaque agent as it is believed to bind to the oral mucosa and is thus retained in the oral cavity for a longer period of time than quaternary ammonium compounds. The use of chlorhexidine in oral preparations however, suffers from the following disadvantages: (1) a prolonged bitter after taste lasting up to several hours; (2) after prolonged use stains are produced on the teeth, tongue, gums, oral mucosa and dental restorations; and (3) production of local irritation of the oral mucosa and tongue.

Inhibition of crystalline HAP formation is usually achieved by compounds which sorb onto a growing crystal and disrupt crystal growth. It is well known in the prior art that water soluble hexametaphosphates, tripolyphosphates and pyrophosphates and the like, are effective calcium and magnesium ion sequestrants and-/or chelating agents. See, for example, U.S. Pat. No. 3,488,419 which discloses oral compositions containing polyphosphate and U.S. Pat. No. 4,215,105 which discloses oral compositions containing phosphonoacetic acid. However, as described in U.S. Pat. No. 4,627,977, the effectiveness of polyphosphates as anticalculus agents has been limited because they are significantly hydrolyzed by salivary enzymes (phosphatases) to orthophosphates which are ineffective as inhibitors of HAP formation. The amount of enzymatic hydrolysis of the polyphosphate has been reduced by the use of a linear molecularly dehydrated polyphosphate salt combined with fluoride as described in U.S. Pat. No. 4,808,410.

Compounds containing a carbon atom covalently bonded to oxygen, the oxygen being covalently bonded to a phosphorous, herein referred to as C-O-P bonds, particularly six C-O-P bonds, such as phytic acid [myo-inositol 1,2,3,4,5,6-hexakis(dihydrogen phosphate)], have been recommended for various purposes in oral compositions. U.S. Pat. Nos. 4,259,316 and 4,335,102 disclose oral anticaries compositions containing a phytate compound and a stannous compound. Due to complex formation between polyvalent cations and phytate anion, the art teaches the presence of stannous compounds in an oral composition containing a phytate compound would not be desirable for inhibition of calculus formation.

In U.S. Pat. No. 3,934,002 phytic acid is disclosed as one of the anticalculus compounds in oral compositions used together with a bisbiguanide antiplaque and anticaries agent. These two agents react with one another so that neither the anticalculus or antiplaque agent would be homogeneously distributed throughout the oral compositions. Since both agents are present, if a mouthrinse is prepared, it contains two visibly distinct phases, one being solid phase reaction product of bisbiguanide and anticalculus agent. U.S. Pat. Nos. 4,263,276 and 4,305,928 also describe visually clear oral compositions containing phytic acid in the presence of an alkali metal fluoride, monofluorophosphate or alkali metal monofluorophosphate, where a cationic material, such as a bisbiguanide or cationic surface active agent can be present. However, effective inhibition of HAP or plaque formation with compositions including compounds containing C-O-P bonds with an antimicrobial have not been known beyond such recommendations or speculation.

It would therefore be desirable to have an oral composition containing an effective antiplaque or anticalculus agent to aid in the prevention of dental caries and gingivitis as well as aid in the control of mouth malodor which does not stain the teeth and does not have a bitter taste. It would also be desirable to provide an antiplaque and anticalculus oral composition in which phytic acid is homogeneously distributed in the oral composition along with a cationic antimicrobial compound.

Furthermore, it would be desirable to provide an oral composition having enhanced retention of cationic antimicrobial compounds on the tooth surfaces useful in the prevention of dental plaque and gingivitis.

SUMMARY OF THE INVENTION

The present invention relates to oral compositions containing phytic acid and a cationic antimicrobial compound and their use for the prevention of dental plaque. In particular, the present invention relates to an oral composition comprising an orally acceptable vehicle containing: (1) from about 0.001 to about 10 percent by weight of one or more compounds having C-O-P bonds, wherein the compound having C-O-P bonds is myo-inositol hexakis(dihydrogen phosphate), myo-inositol pentakis(dihydrogen phosphate), myo-inositol tetrakis(dihydrogen phosphate) or physiologically acceptable salts thereof; (2) from about 0.001 to about 10 percent by weight of one or more cationic antimicrobial compounds; and (3) from about 0.1 to about 20 percent by weight of one or more compatibilizing agents.

A further embodiment of the present invention provides an improved method of inhibiting the formation of dental plaque and/or gingivitis and/or periodontitis and/or aid in controlling oral malodor.

A further embodiment of the present invention provides an oral composition containing phytic acid and a cationic antimicrobial compound which remain in solution, even in the presence of a polyvalent cation or polyvalent cations.

DETAILED DESCRIPTION OF THE INVENTION

The present invention relates to an oral composition consisting essentially of an orally acceptable vehicle containing phytic acid or derivatives thereof, a cationic component and a sufficient amount of a compatibilizing agent to inhibit the phytic acid and antimicrobial compound from interacting to form a precipitate when together in an aqueous solution. An "orally acceptable vehicle" means a medium in which an anticalculus or antiplaque agent may be administered to the oral cavity surfaces without substantial harmful effects to the surfaces thereof.

As plaque is a main etiological factor in gingivitis, periodontitis, tooth decay (dental caries) and other dental associated problems, the ability to control dental plaque aids in preventing and/or controlling gingivitis, periodontitis and dental caries. Thus, as used herein, "antiplaque" means antiplaque and/or antigingivitis and/or antiperiodontitis and/or anticaries. In addition, as the volatile sulfur compounds associated with oral malodor are related to the gingival health, as well as being produced by the putrefactive activity of microorganisms, as used herein, an antiplaque agent will also aid in the control of oral malodor.

To enhance the effect of preventing the formation of dental plaque, it has now been unexpectedly found that the retention of cationic antimicrobial compounds and physiologically acceptable salts thereof to a tooth surface can be substantially enhanced if the cationic antimicrobial compound is used in combination with phytic acid or a derivative thereof in the presence of a sufficient amount of a compatibilizing agent to prevent the phytic acid and cationic antimicrobial compound from interacting to form a precipitate when exposed to each other in an aqueous environment. The ability of an antiplaque agent to remain in contact with the tooth surface to exert an anti-plaque effect is referred to as "substantivity" of the agent. It has also been unexpectedly found that in the presence of a compatibilizing agent, the phytic acid and the cationic antimicrobial compound will remain in solution in the presence of polyvalent cations provided the ratio of polyvalent cation to phytic acid is not greater than about 5 to 1.

In certain preferred forms of the invention, the composition is substantially liquid in character, such as a mouthwash or rinse. In such a preparation the vehicle can be water or a water-alcohol mixture. When using a water-alcohol mixture, the weight ratio of water to alcohol is in the range of from about 1:1 to about 20:1, preferably about 3:1 to about 10:1 and more preferably about 4:1 to about 6:1. The total amount of water or water-alcohol mixture in this type of preparation is typically in the range of from about 70 to about 99.9 percent by weight of the preparation. The pH of such liquid, and other liquid preparations of the invention, is generally in the range of from about 4.5 to about 9, and typically from about 5.5 to about 8. The pH is preferably in the range of from about 6 to about 8.

In certain other desirable forms of this invention, the oral composition may be substantially solid or semisolid in character, such as toothpowder, a dental tablet, a toothpaste, gel or dental cream. The vehicle of such solid or semisolid oral preparation generally contains added polishing material more fully described hereinafter.

As used herein, a "cationic antimicrobial compound" refers to an organic amine where the nitrogen is capable of being positively charged in an aqueous environment, and is represented by one or more of the following general formulae of A-J:

(A) Quaternary ammonium compounds represented by formula I

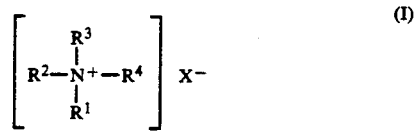

or formula II

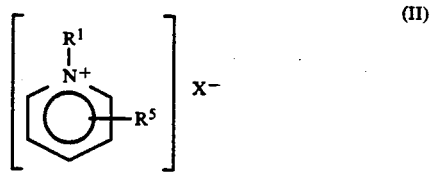

wherein:

$R^1$ is a $C_8$-$C_{20}$ alkyl;

$R^2$ is benzyl or $C_1$-$C_{12}$ alkyl;

$R^3$ and $R^4$ are independently a $C_1$-$C_7$ alkyl or —(CH$_2$—CHOH—CH$_2$—O)$_n$H wherein n is an integer from 1 to 6;

$R^5$ is —H, a $C_1$-$C_7$ alkyl or —(CH$_2$—CHOH—CH$_2$—O)$_n$H wherein n is an integer from 1 to 6; and X⁻ is chloride (Cl⁻), bromide (Br⁻), iodide (I⁻) or fluoride (F⁻);

(B) Pyridinium chlorides containing alkylthiomethyl or alkoxymethyl hydrophobic groups as disclosed by Weglowski et al., *J. Phar. Sci.*, 80; 91-85 (1991), the disclosure of which is hereby incorporated by reference, having the formula $$\left[ \begin{array}{c} \text{pyridinium ring with } CH_2OCH_2CH \text{ substituent and } N^\oplus\text{-}CH_2X^1R^6 \end{array} \right] X^-$$

wherein X is as defined herein before and $X^1$ is oxygen or sulfur; and $R^6$ is a $C_4$-$C_{16}$ alkyl or benzyl;

(C) Quaternary ammonium compounds that are esters of betaine and fatty alcohols, as disclosed by Linstedt et al., *Antimicrobial Agents and Chemotherapy*, 39, 1949-1954 (1990), the disclosure of which is hereby incorporated by reference, having the formula $(CH_3)_3N^\oplus\text{—}CH_2C(O)OR^7$ wherein $R^7$ is a $C_{10}$-$C_{18}$ alkyl; and physiologically acceptable salts thereof;

(D) Sanguinarine and sanguinaria, sanguinaria being an extract from the bloodroot plant *Sanguinaria candensis*, the extract containing benzophenanthridine alkaloids such as sanguinarine, chelerythrine, protopine, homochelidonine and physiologically acceptable salts thereof as disclosed in U.S. Pat. Nos. 4,145,412 and 4,406,881, the disclosures of which are hereby incorporated by reference, sanguinaria being available in dentifrices under the trademark Viadent ™ brand sanguinaria; the major active ingredient sanguinarine chloride salt having the formula

[sanguinarine chloride structure] Cl⁻

(E) Morpholine compounds as disclosed in U.S. Pat. No. 4,894,221, the disclosure of which is hereby incorporate by reference, the morpholine compounds having the formula

[morpholine structure with $R^8$ and $N$—$R^9$]

wherein $R^8$ is a $C_8$-$C_{16}$ alkyl at the 2 or 3 position of the morpholino ring;

$R^9$ is a $C_2$-$C_{10}$ alkyl substituted with a hydroxy group at other than the alpha-position;

the sum of $R_8$ and $R_9$ being greater than or equal to 10 and preferably 10-20; and physiologically acceptable salts thereof;

(F) Antibacterial secondary amines and amides as disclosed in *J. Antibacterial and Antifungal Agents*, 17; 371 (1989), the disclosure of which is hereby incorporated by reference, wherein the antibacterial compounds have the following formulae $R^{10}\text{—NH}\text{—}CH_2CH_2\text{—}N(H)\text{—}CH_2CH_2\text{—}NH_2$ wherein $R^{10}$ is a $C_{10}$-$C_{18}$ alkyl;

$R^{11}\text{—NH}\text{—}CH_2CH_2\text{—}N(H)\text{—}CH_2CH_2\text{—}N(H)\text{—}R^{11}$ wherein each $R^{11}$ is independently $C_8H_{17}$ or $C_{10}H_{21}$;

$R^{13}\text{—C(O)—NH}\text{—}CH_2CH_2\text{—}N(H)\text{—}CH_2CH_2\text{—}NH_2$ wherein $R^{13}$ is a $C_9$-$C_{17}$ alkyl; or $R^{13}C(O)\text{—NH}\text{—}CH_2CH_2\text{—NH—}CH_2CH_2\text{—NCR}^{13}(O)$ wherein each $R^{13}$ is independently $C_7H_{15}$ or $C_9H_{19}$; and physiologically acceptable salts thereof;

(G) Dialkyl amines and N,N'-dialkylpolymethylenediamines as disclosed in *J. Antibacterial and Antifungal Agents*, 17; 579 (1989), the disclosure of which is hereby incorporated by reference, having the formula $R^{14}\text{—NH—}R^{14}$ wherein each $R^{14}$ is independently $C_8H_{17}$ or $C_{12}H_{25}$; or formula $R^{15}\text{—NH}(CH_2)_n\text{NH—}R^{15}$ wherein each $R^{15}$ is independently a $C_7$-$C_{10}$ alkyl; n is an integer from 2 to 5; and physiologically acceptable salts thereof;

(H) N'-Alkyl-N-(2-aminoethyl)piperidine compounds as disclosed by Murata et al., *J. Pharm. Sci.* 80; 26-28 (1991), the disclosure of which is hereby incorporated by reference, the compounds having the formula $R^{16}\text{—NH}(CH_2)_2N$ [piperidine ring]

wherein $R^{16}$ is a $C_{10}$-$C_{18}$ alkyl; and physiologically acceptable salts thereof;

(I) The ammonium compound 4-(2-propylenepentyl)-1-piperidinoethanol described in *J. Periodontal Research*, 18, pp. 429-437 (1983), the compound having the structure $$\left[ (CH_3CH_2CH_2)_2CH\text{—}CH_2\text{—[piperidinium]—}N^\oplus(H)\text{—}CH_2CH_2OH \right] X^-$$

wherein X⁻ is as defined hereinbefore; described in the literature as Octapinal ™ brand 4-(2-propylenepentyl)-1-piperidinoethanol (Ferrosan AB, Sweden); and (J) Alkyl-N-betaine in combination with an alkyl-N,N-dimethylamine oxide; the alkyl-N-betaine having the structure

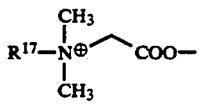

wherein $R^{17}$ is a $C_{10}$–$C_{18}$ alkyl;
the alkyl-N,N-dimethylamine oxide having the structure

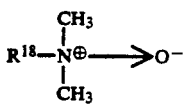

wherein $R^{18}$ is a $C_{10}$–$C_{18}$ alkyl;
as disclosed in U.S. Pat. No. 4,839,158, the disclosure of which is hereby incorporated by reference.

As used herein, the term "alkyl" means a linear or branched alkyl and thus secondary and tertiary alkyls are included. The alkyl terms up to $C_{20}$ include, for example, t-butyl, sec-butyl, isobutyl, and in like manner all such branched or straight chain alkyls.

Preferred quaternary ammonium antibacterial agents include dodecyl trimethyl ammonium bromide, benzyl dimethyl stearyl ammonium chloride, N-tetradecyl-4-ethylpyridinium chloride and cetylpyridinium chloride. The terms antibacterial and antimicrobial mean the ability to inhibit growth, metabolism or reproduction of microorganisms.

The cationic antimicrobial compounds useful in the present invention are commercially available or may be obtained by those of ordinary skill in the art without undue experimentation. For example, quaternary ammonium compounds may be produced by reacting alkyl halides with ammonia or primary amines, or by reacting a tertiary amine, pyridine or pyridine derivative with an alkyl halide. See, for example, Zoltewicz and Deady, *Adv. Heterocycl. Chem.* 22, 71–121 (1978); U.S. Pat. Nos. 2,446,792; 2,295,504 and 4,994,199, the teachings of which are hereby incorporated by reference.

One or more cationic antimicrobial compounds are employed in amounts such that the oral product contains from about 0.001 and 10 percent by weight of the antimicrobial compound. Preferably for desired levels of antiplaque and antigingivitis effect, the finished oral product contains about 0.01 to about 5 percent and preferably about 0.025 to 1.0 percent by weight of the antimicrobial compound. Typically a singular antimicrobial compound is employed in the oral product.

The compounds of the present invention which contain C-O-P bonds are phosphate esters of myo-inositol, such as phytic acid, also known as myo-inositol hexakis(dihydrogen phosphate), inositol hexaphosphoric acid, and 1,2,3,4,5,6-cyclohexanehexaolphosphoric acid. As used herein "phytic acid" means the hexakis phosphate ester of myo-inositol, myo-inositol hexakis(dihydrogen phosphate), and the lesser substituted tetrakis and pentakis phosphate esters of myo-inositol, myo-inositol tetrakis(dihydrogen phosphate) and myo-inositol pentakis (dihydrogen phosphate) respectively, and physiologically acceptable salts thereof, such as alkali metal, alkaline-earth metal, ammonium salts or mixtures thereof. These phytic acid compounds may be used singly or in combination. Phytin, which is the calcium magnesium salt of phytic acid represented by the formula $Ca_5Mg(C_6H_{12}O_{24}P_6.3H_2O)_2$, can also be used in the present invention in addition to or replacement of the phytic acid.

Phytic acid and phytin are commercially available. The tetrakis and pentakis phosphate esters of inositol compounds can be prepared by hydrolyzing sodium phytate with hydrochloric acid and separating the inositol phosphates by high performance liquid chromatography as described by Sanberg and Ahderinne, *J. Food Sci.* 51, 547–550 (1986), the disclosure of which is hereby incorporated by reference.

Phytic acid is present in the oral composition of the present invention, in an amount from about 0.001 to about 10 percent by weight. When the oral composition is essentially liquid in nature, the phytic acid or salt is typically present in an amount from about 0.001 to about 10 percent by weight, preferably from about 0.005 to about 5 percent and more preferably from about 0.01 to about 1 percent by weight.

When the oral composition is essentially liquid in nature, to maintain the cationic antimicrobial compound and phytic acid in solution, it is desirable that the composition contain a sufficient amount of a compatibilizing agent to keep the phytic acid and cationic antimicrobial compound from interacting to form a precipitate. Compatibilizing agents in the present invention are those which do not have a detrimental effect on the substantivity of the cationic antimicrobial compound in the presence of phytic acid and maintains the cationic antimicrobial compound and phytic acid in solution when the oral composition is essentially liquid in nature such that an aqueous solution of the phytic acid, cationic antimicrobial compound and compatibilizing agent does not visually become turbid after standing for 30 minutes at room temperature.

When the oral composition is substantially gel-like or semisolid in form, the vehicle of such solid oral preparation contains a liquid moiety of water so that the phytic acid, cationic antimicrobial compound and compatibilizing agent are homogeniously distributed throughout the liquid phase of the composition. The total amount of water in gel-like or semisolid-like oral compositions is typically in the range of from about 5 to about 60 percent by weight of the preparation, preferably from about 10 to about 50 percent.

While not wishing to be bound by theory, it is believed the compatibilizing agents of the present invention reduce the interaction between the phytic acid and cationic antimicrobial compound, reducing or preventing the formation of a precipitate when these two compounds are exposed to each other in an aqueous environment. The amount of compatibilizing agent in the oral compositions of the present invention is from about 0.1 to about 20 percent by weight, preferably from about 0.1 to about 10 percent by weight of the total composition. Particularly useful compatibilizing agents for oral compositions of the present invention which are substantially liquid in nature are acids and their alkali metal or alkaline-earth metal salts, or mixtures thereof. The mixtures are designated herein as anionic buffers. Suitable anionic buffers are, for example, phosphate, acetate, borate, citrate, bicarbonate, gluconate, tartrate, sulfate, and the like, or mixtures thereof. The preferred anionic buffers being phosphate and bicarbonate. When the oral composition is essentially in the liquid form, the anionic buffer is present in a concentration of from about 0.1M to about 1.0M, preferably from about 0.25M to about 0.75M.

The molar ratio of phytic acid to the cationic antimicrobial compound in the presence of a compatibilizing agent is preferably from about 10:1 to about 1:10, more preferably from about 5:1 to about 1:5, and most preferably about 1:1.

Preparation of the oral compositions of the present invention can be made by using customary procedures for unifying components applied to the teeth and gingiva. It has been found that liquid mouthwashes and topical solutions of the present invention, can be prepared by: (a) dissolving the phytic acid and compatibilizing agent in water, (b) adjusting the pH to between about 6 to about 8, and then (c) adding the cationic antimicrobial compound. When the oral compositions of the present invention contain a polyvalent metal ion in addition to the phytic acid, the compatibilizing agent and the cationic antimicrobial compound, then the compositions are advantageously prepared by: (a) dissolving the metal ion, phytic acid, and a compatibilizing agent in water, (b) adjusting the pH to between about 6 to about 8, and then (c) adding the cationic antimicrobial compound. Alternatively, the cationic antimicrobial compound can be added to the solutions above, prior to adjusting the pH. Other components, such as sweetening and flavoring agents as described more fully herein, can then be added if desired.

To prepare an oral composition which is substantially solid or semisolid in character, an aqueous solution of the phytic acid, cationic antimicrobial compound and compatibilizing agent is prepared in the ratios as described above, and the water removed. Alternatively, a substantially solid or semisolid oral composition containing phytic acid, cationic antimicrobial compound and compatibilizing agent may be prepared by mixing the components in the preferred ratios with the other ingredients of the oral composition as described herein.

It has been unexpectedly found that a metal ion selected from strontium ($Sr^{2+}$), magnesium ($Mg^{2+}$), tin ($Sn^{2+}$), zinc ($Zn^{2+}$), calcium ($Ca^{2+}$) or mixtures thereof, can be added to the oral composition containing the phytic acid, cationic antimicrobial compound and compatibilizing agent without the phytic acid precipitating from solution. The molar ratio of the metal ion to the phytic acid which can be present in the oral compositions of the present invention is from about 4:1 to about 1:4, preferably from about 3:1 to about 1:3, and more preferably about 1:1. The inclusion of a metal ion with the phytic acid and antimicrobial agent would aid in the suppression of oral malodor in addition to aiding in the control of calculus, plaque and gingivitis due to the inhibitory effect of the antimicrobial compound.

The dentifrices of the present invention may also be in a kit form for treating the oral cavity, the kit comprising phytic acid in an orally acceptable vehicle, one or more compatibilizing agents in an orally acceptable vehicle, and one or more cationic antimicrobial compounds in an orally acceptable vehicle; and a means to contain the phytic acid separately from the cationic antimicrobial. Means to separate the phytic acid and cationic antimicrobial includes placing them in separate vessels or in a compartmentalized container. The compatibilizing agent may be mixed with the phytic acid, with the cationic antimicrobial or may be contained separately.

When the dentifrice of the present invention is in a kit form, the phytic acid, compatibilizing agent and cationic antimicrobial compound is mixed prior to application.

When mixing the phytic acid, compatibilizing agent and cationic antimicrobial compound prior to application to the oral cavity, it may be necessary to increase their concentration to account for dilution effects which can occur upon mixing. When applying the phytic acid, compatibilizing agent and cationic antimicrobial in a kit form by mixing prior to use, the concentration of the individual compounds to which the oral cavity is exposed should be in the range given hereinbefore for their concentration in the final dentifrice product.

A variety of other ingredients may be added to the dentifrices of the present invention. Thus for example, prophylactic agents, polishing agents, soaps or detergents, flavoring and sweetening agents, thickening agents and humectants may be included using techniques which are known in the art.

Representative prophylactic agents include supplemental caries-preventing materials such as sodium fluoride, stannous fluoride, potassium fluoride, hexylamine hydrofluoride, myristylamine hdyrofluoride, betaine fluoride, glycine potassium fluoride, etc. A particularly preferred fluoride is sodium fluoride. Typically these prophylactic agents are present in sufficient concentrations so as to provide an available fluoride ion concentration of up to about 2 percent by weight, and preferably in the range of about from 0.5 to about 2 percent by weight, of the dentifrice composition.

Suitable polishing agents include, for example, abrasive materials such as insoluble condensed phosphates such as calcium pyrophosphate, insoluble calcium polyphosphate (also known as calcium polymetaphosphate) and highly polymerized sodium polyphosphate; and water impervious cross-linked thermosetting resins such as the condensations products of melamine and urea with formaldehyde. Other suitable polishing agents will be obvious to those skilled in the art.

The polishing material is generally present in the solid or semisolid compositions in weight concentrations of from about 10 to about 99 percent. Preferably, it is present in amounts ranging from about 20 to about 75 percent in toothpaste, and from about 70 to about 99 percent in tooth powder.

Soaps or detergents may also be employed in the present invention to lower the surface tension to achieve increased prophylactic action, assist in achieving thorough and complete dispersion of the anticalculus agent and render the instant compositions more cosmetically acceptable. Suitable soaps include, for example, the soaps of high molecular weight fatty acids such as sodium and potassium soaps of myristic, stearic or palmitic acids and fatty acids mixtures of palm oil and coconut oil. Typical synthetic detergents include alkyl sulfates and sulfonates having alkyl groups of from about 8 to about 18 carbon atoms, such as, for example, sodium lauryl sulfate, the sulfated fatty alcohols derived from coconut oil and palm oil. The soaps typically comprise up to about 5 percent by weight of the dentifrice composition.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon and orange and methyl salicylate. Suitable sweetening agents include sucrose, lactose, maltose, sorbitol, xylitol, sodium cyclamate, perillartine, APM (aspartylphenylalanine, methyl ester), saccharine and the like. Suitably, flavor and sweetening agents may together comprise from about 0.1 percent to 5 percent of the preparation.

Toothpastes, creams and gels typically contain a natural or synthetic thickener or gelling agent in proportions of from about 0.1 to about 10 percent, preferably from about 0.5 to about 5 percent, by weight. Suitable gelling or thickening agents include for example, water-soluble salts of cellulose ethers such as sodium carboxymethyl cellulose and sodium carboxymethylhydroxyethyl cellulose; natural gums such as gum karaya, gum arabic, and gum tragacanth; and colloidal magnesium aluminum silicate or finely divided silica.

Suitable humectants which may be employed in compositions of the invention include glycerine, propylene glycol, sorbitol, polypropylene glycol and/or polyethylene glycol and other polyhydric alcohols. The humectants may comprise from about 10 to about 90 percent by weight of the dentifrice composition.

The invention will be further clarified by a consideration of the following examples, which are intended to be purely exemplary of the present invention.

GENERAL EXPERIMENTAL

Preparation of Stock Solutions 0.045M phytic acid

A 0.045 molar (M) solution of phytic acid was prepared by dissolving 1.462 g (1.125 millimoles (mMol)) of 50 percent by weight of phytic acid (Jonas Chemical Corp.) in 10 mL of water. The pH of this solution was brought to 7.78 by the addition of 1N NaOH. This solution was transferred quantitatively to a 25 mL volumetric flask and diluted to the mark with water.

0.0045M phytic acid

A 0.0045M solution of phytic acid was prepared by adding 0.743 mL of phytic acid (40 percent weight solution, Aldrich Chemical Co., Inc.) to a 100 mL volumetric flask and diluting to the mark with water.

0.0045M CPC

A 0.0045M solution of cetylpyridinium chloride (CPC) was prepared by adding 0.4026±0.0001 g of CPC (Aldrich Chemical Co., Inc.) to a 250 mL volumetric flask, dissolving in water and diluting to mark with water. The final pH of the solution was 7.4.

0.045M HEDP

A 0.045M solution of hydroxyethylidenediphosphonic acid (HEDP) was prepared by adding 0.0618±0.0001 g of 60 percent active HEDP (MAYO Chemical Co.) to a 60 mL beaker and adding 40 mL of water. This solution was adjusted to pH 7.6 using a few drops of 1.0N sodium hydroxide.

1.5M phosphoric acid

A 1.5M phosphoric acid solution was prepared by adding 25 mL of water to a beaker containing 17.29 g of 85 percent by weight solution of phosphoric acid (Mallinckrodt). The pH of this solution was raised to about 7 with the addition of 50 percent by weight sodium hydroxide. The solution was then transferred quantitatively to a 100 mL volumetric flask and diluted to the mark with water.

Glycolysis pH Test

A sucrose solution was prepared by loading 1.0 g of sucrose (Imperial Pure Cane Sugar) into a 60 mL beaker and then adding 20 mL of water. To this solution was added 8.0 mL of pooled whole human saliva. The saliva was collected from donors who had been permitted to eat or drink anything prior to collection period, but had foregone any oral hygiene on the day of collection. Prior to the collection, each donor rinsed their mouth for thirty seconds with approximately 30 mL water, and after waiting about 5 minutes, began collecting saliva for 30–40 minutes, keeping the collected saliva on ice.

To the saliva/sucrose solution was added 1.0 mL of brain/heart infusion broth containing *Streptococcus mutants* (American Type Culture Collections No. 25175, ATCC) and 1.0 mL of brain/heart infusion broth containing *Streptococcus sanguis* (ATCC #10556). These cultures had been inoculated into 40 mL of broth and grown at 37° C. for sixteen hours prior to adding to the saliva/sucrose solution. (Each broth contained approximately 60 million colony forming units at the time of addition.)

Aliquots of 0.75 mL of the above saliva/sucrose/bacterial solution were added to the test tubes containing various washed HAP suspensions. These test tubes were capped and attached to a tube rotator and placed in a 37° C. incubator for sixteen hours. Following this incubation period, the rotator was removed from the oven and allowed to cool to ambient temperature. The pH of the solutions were checked with a pH meter using a pH electrode calibrated with pH 4, 7 and 10 buffers.

Treating and Washing Hydroxyapatite

To determine the substantivity of CPC in combination with phytic acid, the following washing procedure of the hydroxyapatite was done prior to performing a glycolysis pH test:

A 60 mL beaker was loaded with 12.0 g of hydroxyapatite (HAP) in a buffer suspension (25 percent by weight solids from Sigma Chemical Co.) and washed with 25 mL of water. The HAP suspension was filtered through a medium glass fitted filter to obtain a HAP filter cake. The HAP filter cake was washed a second time with an additional 25 mL of water and then filtered through a glass filter funnel. The white solid filter cake containing 3.0 g of HAP without the buffer was resuspended with 30.0 mL of water to produce a 3.0 g HAP/30.0 mL or 100 mg/mL suspension.

Two mL of the HAP suspension was transferred to each of several sterile-disposable polystyrene 5 mL test tubes labeled $D_1$-$D_n$ (where n=number of test solutions). Two mL of a test solution were then added to each test tube.

The tubes containing the HAP and test solution were capped and attached to a Tube Rotator and rotated end-over-end to allow the test solutions to contact the HAP for a total of ten minutes.

After mixing, the test tubes were placed in an Industrial Equipment Company (IEC) model K centrifuge and spun at setting 25 (mid-range) for ten minutes. The tubes were removed and the liquid layer decanted. A macropipettor was then used to add 3.0 mL of water to each test tube containing the centrifuged hydroxyapatite. The HAP solids were resuspended by vigorous in-and-out flowing action through the pipette. The tubes were again centrifuged at setting 25 for ten minutes and the liquid layer decanted. Following the three milliliter wash step, the HAP solids were resuspended in 2.0 mL of water to produce the original 100 mg/mL suspension concentration. A 0.5 mL sample (containing 50 mg HAP) of this HAP suspension was removed and placed in each of several 5 mL polystyrene test tube labeled $A_1$-$A_n$. This sample A contains one fourth of the original HAP suspension which has been washed with three milliliters of water.

The remaining 1.5 mL in test tubes labeled $D_1$-$D_n$ were centrifuged for ten minutes, the test tubes removed, and the liquid layer decanted. Three milliliters of water were added to these test tubes and the HAP solids resuspended/washed using disposable pipettes. The tubes were centrifuged for ten minutes, the tubes removed and the liquid layer decanted. An additional three milliliters of water were added to these tubes and the HAP solids resuspended/washed by pipette. These tubes were again placed in the centrifuge and spun for ten minutes. The tubes were removed, the liquid layer decanted and 1.5 mL of water added to each tube. The HAP solids were resuspended to the original 100 mg/mL concentration and a 0.5 mL sample removed and placed in each of several 5 mL polystyrene test tubes labeled $B_1$-$B_n$. This sample B contained 50 mg HAP solids which had been treated with test solution and then washed with a total of eleven milliliters of water.

The procedure given above was repeated a third and fourth time to create a series of test tubes labeled $C_1$-$C_n$ and $D_1$-$D_n$. The C samples contained HAP solids which had been treated with test solution and then washed with a total of 18.5 mL of water. The D samples contained HAP solids which had been treated with the test solution and then washed with a total of 25.5 mL water.

A glycolysis pH test was then performed as described above by adding 0.75 aliquots of the saliva/sucrose/bacterial mixture to the test tubes labeled $A_1$-$D_n$, each containing 0.5 mL of the treated washed HAP suspension.

EXAMPLE 1

Incompatibility of CPC with Phytic Acid

Into each of eight vials was placed 500 μL of 0.0045M CPC, varying amounts of a 0.045M phytic acid solution and water as shown in Table I to give a final concentration of 1.5 mM CPC in all the samples. The phytic acid solution and water were combined first.

The vials were then capped and allowed to mix on an end-over-end rotator for 18 hours to allow for complete precipitation. At the end of this time, the tubes were centrifuged at 4,000 rpm for 5 minutes and a 200 μL aliquot of the supernatant removed and added to three mL of water. These diluted samples were then mixed in a quartz cuvette and the ultraviolet absorption determined at 260 nanometers. The amount of CPC still in solution was determined by comparing the absorbance of the samples to the absorbance of a 0.0015M CPC solution. The results, as shown in Table I, show CPC precipitates in the presence of phytic acid.

TABLE I

| μL Phytic Acid | μL Water | mM CPC* | mM Phytic Acid | % of CPC* still in Solution |
|---|---|---|---|---|
| 1000 | 0 | 1.5 | 30 | 21.3 |
| 500 | 500 | 1.5 | 15 | 10.7 |
| 100 | 900 | 1.5 | 3 | 3.5 |

TABLE I-continued

| μL Phytic Acid | μL Water | mM CPC* | mM Phytic Acid | % of CPC* still in Solution |
|---|---|---|---|---|
| 50 | 950 | 1.5 | 1.5 | 1.9 |
| 33.3 | 966.7 | 1.5 | 1.0 | 1.8 |
| 26.7 | 973.7 | 1.5 | 0.8 | 1 |
| 10 | 990 | 1.5 | 0.3 | 2.9 |
| 5 | 995 | 1.5 | 0.15 | 13.4 |

*CPC = cetylpyridinium chloride

EXAMPLE 2

The procedure in Example 1 was repeated except the CPC and phytic acid solutions were made in 0.5M phosphate buffer at pH 7.3. The phosphate buffer was prepared from 85 percent by weight of phosphoric acid and adjusted to pH about 7.3 with 50 percent by weight of sodium hydroxide. The phosphate buffer was also substituted for the water portion of the solutions. The percent of CPC remaining in solution was determined by measuring the ultraviolet absorbence of the samples compared to a 0.0015M CPC standard. The results, given in Table II, show no CPC is precipitated from solution at any of the various concentrations and demonstrate the compatibilization of CPC with phytic acid in the presence of an anionic buffer.

TABLE II

| μL Phytic Acid | μL Phosphate Buffer | mM Phytic Acid | % of CPC* still in Solution |
|---|---|---|---|
| 1000 | 0 | 30 | 105.8 |
| 500 | 500 | 15 | 102.4 |
| 100 | 900 | 3 | 103.2 |
| 50 | 950 | 1.5 | 103.6 |
| 33.3 | 966.7 | 1.0 | 103 |
| 26.7 | 973.3 | 0.8 | 100.4 |
| 10 | 990 | 0.23 | 103.7 |
| 5 | 995 | 0.15 | 101.7 |

*CPC = cetylpyridinium chloride

EXAMPLE 3

Using the experimental procedures described above for glycolysis test and preparation of the hydroxyapatite, the following compounds were tested for HAP substantivity: water (control); cetylpyridinium chloride (CPC); phytin/phosphoric acid/citric acid (PyPCi); hydroxyethylidene phosphate (HEDP); hydroxyethylidene phosphate/cetylpyridinium chloride (HEDP/CPC); and phytin/phosphoric acid/citric acid/cetylpyridinium chloride (PyPCiC). All the compounds tested were 0.0015M except for phosphate and citrate which were 0.015M.

The 0.0015M CPC and 0.0015M HEDP solutions were prepared by diluting 0.0045M stock solutions prepared as previously described.

The PyPC (phytin/phosphate/citrate) solution was prepared by placing 123 mg (75 μmoles) of phytin (American Tokyo Kasei, Inc.) and 4 mL of 0.15M citric acid into a 4 ounce jar. (The citric acid being prepared by adding 1.575 g of citric acid to water and bringing the final volume to 50 mL in a volumetric flask). To this suspension of phytin and citric acid was added 2.873 g (0.025 mole) of neat phosphoric acid followed by 30 mL of water. The pH was adjusted to 7.38 by the addition of 50 percent by weight of sodium hydroxide. After allowing the solution to cool to room temperature, an additional 10 mL of water was added to bring the volume to 50 mL. The pH was 7.36. The solution had a faint turbidity and was centrifuged and the supernatant decanted giving a clear solution.

The PyPCiC (phytin/phosphate/citrate/cetylpyridinium chloride) solution was prepared by placing 5.37 mg of CPC into a 10 mL volumetric flask and bringing to the 10 mL mark using the phytin/phosphate/citrate solution described above.

The HEDP/CPC (hydroxyethylidene phosphate/cetylpyridinium chloride solution) was prepared by placing 20 mL of a 0.0045M HEDP solution into a 4 ounce jar and adding 20 mL of water and 20 mL of a 0.0045M CPC stock solution. The pH was adjusted to 7.4 with the dropwise addition of 1.0N sodium hydroxide.

The phosphate buffer/CPC (Phos/CPc) solution was prepared by adding 20 mL of a 0.042M sodium phosphate buffer solution to a four ounce jar and diluting with 20 mL of water and 20 mL of a 0.0045M CPC stock solution. The 0.042M sodium phosphate buffer was prepared by adding 0.2318±0.0001 g of $NaH_2PO_4 \cdot H_2O$ (J. T. Baker Chemical Co.) to a 60 mL beaker and adding 40 mL of water and adjusting the pH to 7.36 by the dropwise addition of 1N sodium hydroxide.

The results of the glycolysis pH test for HAP treated by the above compounds are shown Table III.

TABLE III

| | pH as a Function of HAP Washings | | | | | |
|---|---|---|---|---|---|---|
| Volume of Wash (mL) | Water | CPC[1] | PyPCi[2] | HEDP[3] | HEDP/CPC[4] | Phos/CPC[5] | PyPCiC[6] |
| 3 | 5.04 | 6.98 | 5.07 | 5.04 | 7.04 | 7.02 | 7.3 |
| 11 | 5.12 | 5.29 | 5.12 | 5.5 | 5.87 | 5.84 | 7.01 |
| 18.5 | 5.06 | 5.13 | 5.18 | 5.21 | 5.3 | 5.18 | 7.04 |
| 25.5 | 5.14 | 5.35 | 5.2 | 5.15 | 5.29 | 5.1 | 7.04 |

[1]CPC = cetylpyridinium chloride
[2]PyPCi = phytin, phosphate and cetylpyridinium chloride
[3]HEDP = hydroxyethylidene phosphate
[4]HEDP/CPC = hydroxyethylidene phosphate and cetylpyridinium chloride
[5]Phos/CPC = phosphate and cetylpyridinium chloride
[6]PyPCiC = phytin, phosphate, citrate and cetylpyridinium chloride These results show that retention of cetylpyridinium chloride as measured by the retention of antimicrobial activity was greatest for the PyPCiC solution.

EXAMPLE 4

Using the experimental procedures described above for the glycolysis test and preparation of the hydroxyapatite, the following compounds were tested for HAP substantivity: water (control); cetylpyridinium chloride (CPC); phytin/phosphoric acid/citric acid/cetylpyridinium chloride (PyPCiC); and phytic acid/phosphoric acid/citric acid/cetylpyridinium chloride (PaPCiC). The CPC and PyCiC solutions were prepared as given in Example 3. The phytic acid/phosphoric acid/citric acid/cetylpyridinium chloride (PaPCiC) solution was prepared by adding 77.2 μL (150 μmoles) of phytic acid (40 percent by weight, Aldrich Chemical Co., Inc.), 2.873 g of phosphoric acid, 4 mL of 0.15M citric acid and 25 mL water to a vial. This solution was brought to pH 7.39 by the addition of 3.71 g of 50 percent by weight of sodium hydroxide and diluted to mark with water in a 50 mL volumetric flask. A 5.37 mg portion of CPC was dissolved in 10 mL of this solution to produce a solution containing 3 mM phytic acid, 12 mM citrate, 1.5 mM CPC and 500 mM phosphate.

The results of the glycolysis pH test for HAP treated by the above compounds are shown in Table IV.

TABLE IV

| | pH as a Function of HAP Washing | | | |
|---|---|---|---|---|
| Volume of Wash (mL) | Water | CPC[1] | PyPCiC[2] | PaPCiC[3] |
| 3 | 4.83 | 7.12 | 7.34 | 7.40 |
| 11 | 4.91 | 6.02 | 7.07 | 7.14 |
| 18.5 | 4.93 | 5.15 | 7.18 | 7.22 |
| 25.5 | 5.17 | 5.35 | 7.17 | 7.24 |

[1]CPC = cetylpyridinium chloride
[2]PyPCiC = phytin, phosphate, citrate and cetylpyridinium chloride
[3]PaPCiC = phytic acid, phosphate, citrate and cetylpyridinium chloride These results show that both phytin and phytic acid enhance the substantivity of CPC to hydroxyapatite as measured by the glycolysis pH test.

EXAMPLE 5

Preparation of the HAP and the treatment of the HAP with test solutions was as described under general experimental. However, the amount of water wash of the HAP suspensions was increased from three to 10 mL. As a result, samples A, B, C and D were removed after washing with 10, 31, 51.5 and 71.5 mL of water, respectively. Using this wash procedure, the solutions as prepared in Example 4 were tested for HAP substantivity: water (control); cetylpyridinium chloride (CPC); phytin/phosphoric acid/citric acid/cetylpyridinium chloride (PyPCiC); phytic acid/phosphoric acid/citric acid/cetylpyridinium (PaPCiC).

The results of the glycolysis pH test for HAP treated by the above compounds are shown in Table V.

TABLE V

| | pH Drop as a Function of HAP Washings | | | |
|---|---|---|---|---|
| mL of Water Wash | Water | CPC[1] | PyPCiC[2] | PaPCiC[3] |
| 10 | 4.76 | 7.15 | 7.32 | 7.26 |
| 31 | 4.83 | 5.04 | 7.24 | 7.21 |
| 51.5 | 4.88 | 5.01 | 7.34 | 7.30 |
| 71.5 | 5.19 | 5.17 | 7.36 | 7.28 |

[1]CPC = cetylpyridinium chloride
[2]PyPCiC = phytin, phosphate, citrate and cetylpyridinium chloride
[3]PaPCiC = phytic acid, phosphate, citrate and cetylpyridinium chloride The results show that retention of cetylpyridinium chloride as measured by the retention of antimicrobial activity was substantially enhanced by the presence of phytic acid or phytin and an anionic buffer under extended washing procedures.

EXAMPLE 6

Using the wash procedure of 10, 31, 51.5 and 71.5 mL of Example 5, the following compounds were tested for HAP substantivity: water (control); cetylpyridinium chloride (CPC); phytic acid/phosphoric acid/cetylpyridinium chloride (PaPC). The CPC was 0.0015M as described in Example 3. The PaPC solution was prepared by adding 92.6 μL of phytic acid (40 percent weight solution, Aldrich Chemical Co., Inc.) and 20 mL of water to a 100 mL beaker. To this solution was added 3.45 g of phosphoric acid (85 percent by weight solution, Mallinckrodt) and the pH adjusted to 7.4 with the dropwise addition of 0.85 g of 50 percent by weight sodium hydroxide solution. The volume of the solution was then brought to 40 mL. This phytic/phosphate buffer solution was then formulated with 20 mL of 0.0045M CPC stock solution to produce a formulation containing 0.0012M phytic acid, 0.5M phosphate buffer, 0.0015M cetylpyridinium chloride. The results of the glycolysis pH test for HAP treated by the above compounds are shown in Table VI.

TABLE VI

| mL of Water Wash | pH as a Function of HAP Washings | | |
|---|---|---|---|
| | WATER | CPC[1] | PaPC[2] |
| 10 | 5.29 | 7.38 | 7.59 |
| 31 | 5.29 | 5.55 | 7.49 |
| 51.5 | 5.29 | 5.43 | 7.41 |
| 71.5 | 5.21 | 5.33 | 7.54 |

[1]CPC = cetylpyridinium chloride

[2]PaCP = phytic acid, phosphate and cetylpyridinium chloride

The results show that retention of cetylpyridinium chloride as measured by the retention of antimicrobial activity is substantially enhanced during extended water washing by the presence of phytic acid with only phosphate buffer to compatibilize the phytic acid and cetylpyridinium chloride.

EXAMPLE 7

The preparation of the HAP and the treatment of the HAP with test solutions was as previously described except in addition to using a 10 mL wash, the number of washing steps was doubled. Thus samples A, B, C and D are thus removed after washing with 22, 63.5, 84.5 and 105 mL respectively. Using this procedure, the following compounds were tested for HAP substantivity: water (control); cetylpyridinium chloride (CPC); and the following metals with phytic acid/phosphate/cetylpyridinium chloride: calcium: (Ca-PaPC); magnesium (Mg-PaPC); tin (Sn-PaPC); zinc (Zn-PaPC); strontium (Sr-PaPC); and copper (Cu-PaPC). The CPC was prepared as in Example 3. The formulations containing the metals were prepared by weighing into labeled jars the amount of metal chloride as given in Table VII.

TABLE VII

Preparation of Metal Chloride Solutions

| Metal | Formula | Wt. (g) added to jar | FW* |
|---|---|---|---|
| Calcium | CaCl$_2$.H$_2$O | 0.0298 | 147.02 |
| Zinc | ZnCl$_2$ | 0.0277 | 136.28 |
| Strontium | SrCl$_2$.6H$_2$O | 0.0540 | 266.62 |
| Tin | Sn(II)Cl$_2$.2H$_2$O | 0.0457 | 225.63 |
| Magnesium | MgCl$_2$.6H$_2$O | 0.0411 | 203.31 |
| Copper | CuCl$_2$ | 0.0273 | 134.45 |

*FW = formula weight

A 15 mL aliquot of a 0.0045M phytic acid solution and a 15 mL aliquot of a 1.5M phosphoric acid solution were then added to each jar and the pH adjusted to about 7 with the dropwise addition of 50 percent sodium hydroxide. A 15 mL aliquot of a 0.0045M CPC solution was then added to each of the above solutions to produce formulations containing 0.0015M metal; 0.0015M phytic acid; 0.5M phosphate; and 0.0015M CPC. The solutions containing zinc, strontium or copper were initially water clear, with a precipitate observed after several hours.

The HAP substantivity of the formulations containing the metal as measured by the glycolysis pH test are given in Table VIII.

TABLE VIII

| Volume of Wash (mL) | pH as a Function of HAP Washings[1] | | | | | | | |
|---|---|---|---|---|---|---|---|---|
| | Water | CPC | Ca—PaPC | Mg—PaPC | Sn—PaPC | Zn—PaPC | Sr—PaPC | Cu—PaPC |
| 22 | 5.12 | 5.92 | 7.59 | 7.56 | 7.55 | 7.61 | 7.62 | 7.61 |
| 63.5 | 5.22 | 5.24 | 7.67 | 7.66 | 7.64 | 7.71 | 7.72 | 7.66 |
| 84.5 | 5.33 | 5.34 | 7.75 | 7.77 | 7.69 | 7.78 | 7.81 | 7.73 |
| 105 | 5.43 | 5.44 | 7.76 | 7.80 | 7.73 | 7.82 | 7.84 | 7.76 |

[1]CPC = cetylpyridinium chloride; PaPC = phytic acid, phosphate and cetylpyridinium chloride; Ca = calcium; Mg = magnesium; Sn = Tin; Zn = zinc; Sr = strontium; Cu = copper(II)

These results show that the presence of metal ions does not interfere with the ability of phytic acid to enhance the substantivity of CPC to hydroxyapatite.

EXAMPLE 8

The following formulations were tested to determine the substantivity of cetylpyridinium chloride to HAP that had been treated with the test compounds in a separate step, prior to exposing the HAP to the cetylpyridinium chloride; water (control); phytic acid; sodium phosphate (NaH$_2$PO$_4$); and tin/phytic acid/phosphate (Sn-PaP). The phytic acid was used at 0.0015M and prepared from a 0.045M stock solution by removing a 5 mL aliquot to a vial and diluting with 10 mL of water. The pH of this solution was 2.5. The tin/phytic acid solution in 0.5M phosphate buffer was prepared by weighing 0.0051±0.0001 g SnCl$_2$ into a vial and brought into solution by the addition of 5 mL of water. A 5 mL aliquot of 0.0045M phytic acid and a 5 mL aliquot of 1.5M phosphate buffer were added to the tin solution to produce a formulation with 0.0015M Sn; 0.0015M phytic acid; and 0.5M phosphate.

The HAP was prepared as described under general experimental and was treated with 2 mL of the test solutions containing phytic acid as indicated above. The HAP solids were then washed with 2-three mL portions of water and then exposed to 2 mL of 0.0015M CPC solution. The HAP suspensions were then washed using the extended wash procedure of 22, 63.5, 84.5 and 105 mL described in Example 7.

The substantivity of the formulations as measured by the glycolysis pH test are given in Table IX.

TABLE IX

| Volume of Wash (mL) | pH as a Function of HAP Washings | | | |
|---|---|---|---|---|
| | Water | Phytic Acid | NaH$_2$PO$_4$ | Sn—PaP* |
| 22 | 5.39 | 7.44 | 7.28 | 7.21 |
| 63.5 | 5.24 | 7.81 | 5.19 | 7.39 |
| 84.5 | 5.28 | 7.52 | 5.26 | 7.51 |
| 105 | 5.32 | 7.47 | 5.25 | 7.41 |

*Sn—PaP = tin, phytic acid and phosphate

The results show that the addition of tin does not interfere with the beneficial effect of phytic acid even with extended washing of the HAP. These results also show the beneficial effects of phytic acid and tin/phytic acid can be exerted by a two step exposure of the HAP.

EXAMPLE 9

In this trial, the preparation of HAP and the treatment of HAP with the test solutions were as previously described under general experimental. The following solutions were tested for HAP substantivity as measured by the glycolysis pH test:
A. Water (control); cetylpyridinium chloride (CPC);
B. Copper/phytic acid/sodium bicarbonate (CuPab);
C. Cetylpyridinium chloride/sodium bicarbonate (CPCB);
D. N-tetradecyl-4-ethylpyridinium bromide (TDEP);
E. Copper/phytic acid/sodium bicarbonate/cetylpyridinium chloride (Cu-PaBC);
F. Phytic acid/sodium bicarbonate/cetylpyridinium chloride (PaBC);
G. Copper/phytic acid/sodium bicarbonate/N-tetradecyl-4-ethylpyridinium bromide (Cu-PaBT).

The concentration of the components being 0.0015M except sodium bicarbonate at 0.5M.

A 0.0045M solution of N-tetradecyl-4-ethylpyridinium bromide was prepared by adding 0.0173±0.0001 g of N-tetradecyl-4-ethylpyridinium bromide to a 10 mL volumetric flask and diluting to mark with water.

The results from this trial are given in Table X.

TABLE X

| VOLUME OF WASH (mL) | pH as a Function of HAP Washings | | | | | | | |
|---|---|---|---|---|---|---|---|---|
| | Samples | | | | | | | |
| | Water | CPC[1] | CuPaB[2] | CB[3] | TDEP[4] | Cu—PaBC[5] | PaBC[6] | Cu—PaBT[7] |
| 3 | 5.23 | 7.71 | 8.01 | 8.78 | 7.82 | 8.62 | 8.78 | 8.73 |
| 13 | 5.27 | 7.80 | 6.05 | 8.53 | 5.42 | 8.36 | 8.50 | 8.39 |
| 21 | 5.30 | 6.73 | 5.82 | 5.73 | 5.32 | 8.23 | 8.37 | 8.26 |
| 31 | 5.34 | 5.43 | 5.84 | 6.05 | 5.39 | 8.19 | 8.25 | 8.14 |

[1]CPC = cetylpyridinium chloride;
[2]CuPaB = copper, phytic acid and sodium bicarbonate;
[3]CB = cetylpyridinium chloride and sodium bicarbonate;
[4]TDEP = N-tetradecyl-4-ethylpyridinium bromide;
[5]Cu—PaBC = copper, phytic acid, sodium bicarbonate and cetylpyridinium chloride;
[6]PaBC = phytic acid, sodium bicarbonate, and cetylpyridinium chloride;
[7]Cu—PaBT = copper, phytic acid, sodium bicarbonate and N-tetradecyl-4-ethylpyridinium bromide The results show that sodium bicarbonate works as effectively in combination with phytic acid and cetylpyridinium chloride as does the phosphate buffer. In addition ethyltetradecylpyridinium bromide works as well as cetylpyridinium chloride as an antimicrobial in combination with phytic acid, copper and bicarbonate buffer.

EXAMPLE 10

An in-vivo study was conducted to determine the ability of the test formulations containing phytic acid to inhibit the experimental formation of gingivitis in Beagle dogs.

Purebred female Beagle dogs, 2–3 years old, with naturally occurring gingivitis were randomly divided into groups of four animals each. After 14 days of adaptation, the teeth of the dogs were scaled to remove supragingival calculus and polished. One week following the prophylaxes, during which time oral care was maintained by brushing, a baseline gingivitis index was obtained as measured by the procedure of Loe, *J. Periodontol.* 38, 610 (1967) and Loe and Silness, *Acta OdontScand* 21, 533 (1963). After the initial gingivitis index reading, the teeth of each group were sprayed twice daily, five days per week, with approximately 10 mL of one of the following mouth rinses:
(A) cetylpyridinium chloride (CPC);
(B) zinc/phytic acid/cetylpyridinium chloride/phosphate;
(C) copper/phytic acid/cetylpyridinium chloride/bicarbonate;
(D) tin/phytic acid/cetylpyridinium chloride/phosphate;
(E) phytic acid/cetylpyridinium chloride/phosphate.

All components were present at a concentration of 0.0015M except the phosphate and bicarbonate at 0.5M and the metals which were at 0.0014M.

After four weeks of treatment, the gingival index was again measured. The results given in Table XI showing the increase in the gingival index, show that the phytic acid/cetylpyridinium chloride/phosphate composition was the most effective composition of those tested for inhibiting deterioration of the gingival health. The phytic acid containing test solutions gave a lower increase in the gingival index when compared to the cetylpyridinium chloride alone.

TABLE XI

| Formulation[a] | Change in Gingival Index over 4 weeks |
|---|---|
| CPC | 0.528 |
| Zn-phytic/CPC/phos | 0.479 |
| Cu-phytic/CPC/bicarb | 0.430 |
| Sn-phytic/CPC/phos | 0.349 |
| phytic/CPC/phos | 0.199 |

[a]CPC = cetylpyridinium chloride; phytic = phytic acid; phos = phosphate; bicarb = bicarbonate

EXAMPLE 11

Retention of CPC on Hydroxyapatite

To separate tubes containing (1) 4.5 mM cetylpyridinium chloride (CPC); (2) 4.5 mM phytic acid, 4.5 mM CPC, and 0.5M phosphate, pH 7.47; and (3) 4.5 mM CPC in 0.5M phosphate was added 100 mg of washed hydroxyapatite (added as 1 mL of 100 mg/mL suspension in water). The suspensions were mixed for 10 minutes, centrifuged, a 200 μL aliquot of the supernatant removed and diluted with 3.0 mL of water, and the absorbance of the diluted aliquot measured at 260 nanometers.

The supernatant remaining in each tube was carefully removed and the remaining hydroxyapatite resuspended in 3.0 mL of water and mixed for 10 minutes. The suspensions were again centrifuged and a 200 μL aliquot of the supernatant removed, diluted and ultraviolet absorbance measured at 260 nanometers. The supernatant was discarded after the absorbance reading. The procedure of resuspending the hydroxyapatite in 3 mL of water, mixing, centrifuing and measuring the absorbance of the supernatant was repeated an additional six times. By knowing how much CPC was adsorbed onto the hydroxyapatite and how much was being removed in each wash, the number of washes necessary to completely remove the CPC from the hydroxyapatie was estimated. The results from this trial are given in Table XII.

TABLE XII

| Sample | Percent of *CPC initially adsorbed onto hydroxyapatite | Number of water washed to remove all CPC from hydroxyapatite |
|---|---|---|
| CPC | 37 | 14 |
| Phytic acid/CPC | 75 | 24 |
| Phosphate/ CPC | 25 | 14 |

*CPC = cetylpyridinium chloride

The results show that a compound of the present invention containing C-O-P bonds, such as phytic acid, increases the amount of CPC which is adsorbed onto the hydroxyapatite and causes the CPC to be desorbed at a lower rate.

EXAMPLE 12

Compatibility of Calcium with Phytic Acid and CPC in the Presence of Phosphate

To determine the compatibility of metal ions with phytic acid and cetylpyridinium chloride (CPC) in the presence of a phosphate buffer, a 0.0012M solution of phytic acid was prepared in 0.5M phosphate buffer (pH 7.32) containing 0.0015M CPC. To separate 100 μL aliquots of this solution was added 15, 30, 45, 60 or 75 μL of a 0.01M calcium chloride solution. This gave varying ratios of calcium to phytic acid in the presence of CPC in phosphate buffer. The results are given in Table XIII and show the compatibilizing effect of phosphate buffer on CPC/phytic acid solutions when exposed to calcium ions.

TABLE XIII

| μL of 0.01 M CaCl₂ | Molar ratio of Phytic acid:Ca:CPC* | Observation |
|---|---|---|
| 15 | 1:1.25:1.25 | clear |
| 30 | 1:2.5:1.25 | clear |
| 45 | 1:3.75:1.25 | clear |
| 60 | 1:5:1.25 | slightly turbid |
| 75 | 1:6.25:1.25 | turbid |

*CPC = cetylpyridinium chloride

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. An oral composition consisting essentially of: (1) from about 0.001 to about 10 percent by weight of one or more compounds having C-O-P bonds wherein the compound having C-O-P bonds is myo-inositol hexakis(dihydrogen phosphate), myo-inositol pentakis(dihydrogen phosphate), myo-inositol tetrakis(dihydrogen phosphate) or physiologically acceptable salts thereof; (2) from about 0.001 to about 10 percent by weight of one or more cationic antimicrobial compounds with the proviso that the cationic antimicrobial compounds are other than the chlorhexidine, alexidine or a cationic bisbiguanide compound; (3) from about 0.1 to about 20 percent by weight of a compatibilizing agent and (4) the remaining percent by weight is an orally acceptable vehicle having a pH in the range of about 4.5 to about 9 wherein the compatibilizing agent prevents the phytic acid and antimicrobial compound from forming a precipitate when in an aqueous environment.

2. The composition of claim 1 wherein the cationic antimicrobial compound is one or more quaternary ammonium compounds selected from the group consisting of formula I

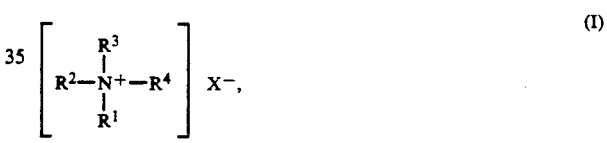

formula II

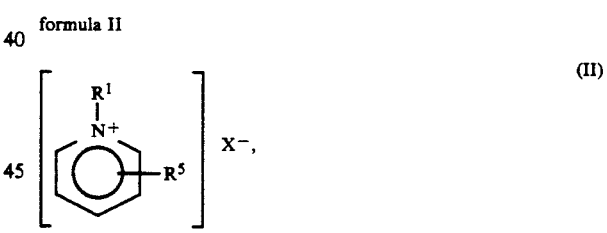

and a mixture thereof;
wherein
R¹ is a $C_8$-$C_{20}$ alkyl,
R² is benzyl or $C_1$-$C_{12}$ alkyl,
R³ and R⁴ are independently a $C_1$-$C_7$ alkyl or —(CH₂—CHOH—CH₂—O)$_n$H wherein n is an integer from 1 to 6,
R⁵ is —H, a $C_1$-$C_7$ alkyl or —(CH₂—CHOH—CH₂—O)$_n$H wherein n is an integer from 1 to 6, and
X⁻ is chloride, bromide, iodide or fluoride.

3. The composition of claim 1 wherein the compound having C-O-P bonds is myo-inositol hexakis(dihydrogen phosphate) or a physiologically acceptable salt thereof.

4. The composition of claim 3 wherein the cationic antimicrobial compound is a quaternary ammonium compound represented by Formula II as defined in claim 2.

5. The composition of claim 4 wherein the quaternary ammonium compound is cetylpyridinium chloride.

6. The composition of claim 4 wherein the quaternary ammonium compound is N-tetradecyl-4-ethylpyridinium chloride.

7. The composition of claim 1 wherein the compatibilizing agent an anionic buffer, wherein the anionic buffer is phosphate, acetate, borate, citrate, bicarbonate, gluconate, tartrate, sulfate or mixtures thereof.

8. The composition of claim 7 wherein the anionic buffer is phosphate, bicarbonate or a mixture thereof.

9. The composition of claim 8 wherein the orally acceptable vehicle contains from about 70 to about 99.9 percent by weight water or an alcohol-water mixture wherein the C-O-P compound is myo-inositol hexakis(dihydrogen phosphate) or a physiologically acceptable salt thereof and the cationic antimicrobial compound is cetylpyridinium chloride.

10. A method of inhibiting dental calculus comprising administering to mammalian teeth a calculus-inhibiting amount of an anticalculus oral composition consisting essentially of: (1) about 0.001 to about 10 percent by weight of one or more compounds having C-O-P bonds wherein the compound having C-O-P bonds is myo-inositol hexakis(dihydrogen phosphate), myo-inositol pentakis(dihydrogen phosphate), myo-inositol tetrakis(dihydrogen phosphate) or physiologically acceptable salts thereof; (2) from about 0.001 to about 10 percent by weight of one or more cationic antimicrobial compounds with the proviso that the cationic antimicrobial compounds are other than chlorhexidine, alexidine or a cationic bisbiguanide compound; (3) from about 0.1 to about 20 percent by weight of a compatibilizing agent and (4) the remaining percent by weight is an orally acceptable vehicle having a pH in the range of about 4.5 to about 9 wherein the compatibilizing agent prevents the phytic acid and antimicrobial compound from forming a precipitate when in an aqueous environment.

11. The method of claim 10 wherein the cationic antimicrobial compound is one or more quaternary ammonium compounds selected from the group consisting of formula I

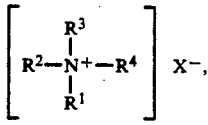

formula II

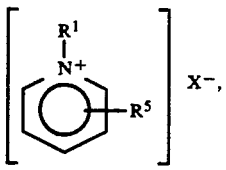

and a mixture thereof;
wherein
R¹ is a C₈-C₂₀ alkyl,
R² is benzyl or C₁-C₁₂ alkyl,
R³ and R⁴ are independently a C₁-C₇ alkyl or —(CH₂—CHOH—CH₂—O)ₙH wherein n is an integer from 1 to 6,
R⁵ is —H, a C₁-C₇ alkyl or —(CH₂—CHOH—CH₂—O)ₙH wherein n is an integer from 1 to 6, and
X— is chloride, bromide, iodide or fluoride.

12. The method of claim 10 wherein the compound having C-O-P bonds is myo-inositol hexakis(dihydrogen phosphate) or a physiologically acceptable salt thereof.

13. The method of claim 12 wherein the cationic antimicrobial compound is a quaternary ammonium compound represented by Formula II as defined in claim 11.

14. The method of claim 13 wherein the quaternary ammonium compound is cetylpyridinium chloride.

15. The method of claim 13 wherein the quaternary ammonium compound is N-tetradecyl-4-ethylpyridinium chloride.

16. The method of claim 10 wherein the compatibilizing agent is an anionic buffer, wherein the anionic buffer is phosphate, acetate, borate, citrate, bicarbonate, gluconate, tartrate, sulfate or mixtures thereof.

17. The method of claim 16 wherein the anionic buffer is phosphate, bicarbonate or a mixture thereof.

18. The method of claim 17 wherein the orally acceptable vehicle contains from about 70 to about 99.9 percent by weight water or an alcohol-water mixture wherein the compound having C-O-P bonds is myo-inositol hexakis(dihydrogen phosphate) or a physiologically acceptable salt thereof and the cationic antimicrobial compound is cetylpyridinium chloride.

19. A method of inhibiting dental plaque and/or oral malodor comprising administering to mammalian teeth a plaque-inhibiting amount of an antiplaque oral composition consisting essentially of: (1) from about 0.001 to about 10 percent by weight of one or more compounds having C-O-P bonds wherein the compound having C-O-P bonds is myo-inositol hexakis(dihydrogen phosphate), myo-inositol pentakis(dihydrogen phosphate), myo-inositol tetrakis(dihydrogen phosphate) or physiologically acceptable salts thereof; (2) from about 0.001 to about 10 percent by weight of one or more cationic antimicrobial compounds with the proviso that the cationic antimicrobial compounds are other than chlorhexidine, alexidine or a cationic bisbiguanide compound; (3) from about 0.1 to about 20 percent by weight of a compatibilizing agent and (4) the remaining percent by weight is an orally acceptable vehicle having a pH in the range of about 4.5 to about 9 wherein the compatibilizing agent prevents the phytic acid and antimicrobial compound from forming a precipitate when in an aqueous environment.

20. The method of claim 19 wherein the cationic antimicrobial compound is one or more quaternary ammonium compounds selected from the group consisting of Formula I

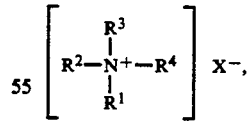

formula II

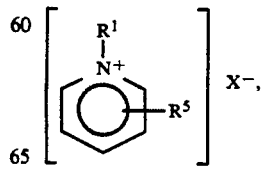

and a mixture thereof;
wherein $R^1$ is a $C_8$-$C_{20}$ alkyl, $R^2$ is benzyl or $C_1$-$C_{12}$ alkyl, $R^3$ and $R^4$ are independently a $C_1$-$C_7$ alkyl or —(CH$_2$—CHOH—CH$_2$—O)$_n$H wherein n is an integer from 1 to 6, $R^5$ is —H, a $C_1$-$C_7$ alkyl or —(CH$_2$—CHOH—CH$_2$—O)$_n$H wherein n is an integer from 1 to 6, and $X^-$ is chloride, bromide, iodide or fluoride.

21. The method of claim 19 wherein the compound having C-O-P bonds is myo-inositol hexakis(dihydrogen phosphate) or a physiologically acceptable salt thereof.

22. The method of claim 21 wherein the cationic antimicrobial compound is a quaternary ammonium compound represented by Formula II as defined in claim 20.

23. The method of claim 22 wherein the quaternary ammonium compound is cetylpyridinium chloride.

24. The method of claim 22 wherein the quaternary ammonium compound is N-tetradecyl-4-ethylpyridinium chloride.

25. The method of claim 19 wherein the compatibilizing agent is an anionic buffer, wherein the anionic buffer is phosphate, acetate, borate, citrate, bicarbonate, gluconate, tartrate, sulfate or mixtures thereof.

26. The method of claim 25 wherein the anionic buffer is phosphate, bicarbonate or a mixture thereof.

27. The method of claim 26 wherein the compound having C-O-P bonds is myo-inositol hexakis(dihydrogen phosphate) or a physiologically acceptable salt thereof, the cationic antimicrobial compound is cetylpyridinium chloride and the buffer is phosphate.

28. The method of claim 27 wherein the orally acceptable vehicle contains from about 70 to about 99.9 percent by weight water or an alcohol-water mixture.

29. The method of claim 26 wherein the compound having C-O-P bonds is myo-inositol hexakis(dihydrogen phosphate) or a physiologically acceptable salt thereof, the cationic antimicrobial compound is cetylpyridinium chloride and the buffer is bicarbonate.

30. The method of claim 29 wherein the orally acceptable vehicle contains from about 70 to about 99.9 percent by weight water or an alcohol-water mixture.

31. The method of claim 26 wherein the orally acceptable vehicle contains from about 70 to about 99.9 percent by weight water or an alcohol-water mixture wherein the compound having C-O-P bonds is myo-inositol hexakis(dihydrogen phosphate) or a physiologically acceptable salt thereof, the cationic antimicrobial compound is cetylpyridinium chloride, and the buffer is bicarbonate.

32. A process for preparing an oral composition as defined in claim 1 comprising the steps of (a) dissolving the compound having C-O-P bonds and the compatibilizing agent in water; and (b) dissolving the cationic antimicrobial compound or a solution of the cationic antimicrobial compound in the solution obtained from step a, wherein the pH of the solution is adjusted to between about 6 and about 8 after step a or step b.

* * * * *